(12) United States Patent
Juhas et al.

(10) Patent No.: US 11,759,126 B2
(45) Date of Patent: Sep. 19, 2023

(54) SCORING METRIC FOR PHYSICAL ACTIVITY PERFORMANCE AND TRACKING

(71) Applicant: Smith & Nephew, Inc., Memphis, TN (US)

(72) Inventors: Brett Juhas, San Diego, CA (US); Sudipto Sur, San Diego, CA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 17/846,558

(22) Filed: Jun. 22, 2022

(65) Prior Publication Data

US 2022/0319236 A1    Oct. 6, 2022

Related U.S. Application Data

(63) Continuation of application No. 16/880,693, filed on May 21, 2020, now Pat. No. 11,403,882.

(Continued)

(51) Int. Cl.
*G06K 9/00* (2022.01)
*A61B 5/11* (2006.01)
(Continued)

(52) U.S. Cl.
CPC .......... *A61B 5/1118* (2013.01); *G06F 18/22* (2023.01); *G06T 7/20* (2013.01); *G06T 7/70* (2017.01); *G06V 10/761* (2022.01); *G06V 40/10* (2022.01); *G06V 40/107* (2022.01); *G06V 40/23* (2022.01); *G06T 2207/30196* (2013.01)

(58) Field of Classification Search
None
See application file for complete search history.

(56) References Cited

U.S. PATENT DOCUMENTS 9,011,293 B2    4/2015  Shavit et al.
9,154,739 B1   10/2015  Nicolaou et al.
(Continued)

FOREIGN PATENT DOCUMENTS

AU      2017386412 A1    6/2019
CA       2554428 A1    8/2005
(Continued)

OTHER PUBLICATIONS

International Search Report and Written Opinion for the International Patent Application No. PCT/US2020/034096, dated Sep. 9, 2020, 7 pages.

(Continued)

*Primary Examiner* — Soo Jin Park
(74) *Attorney, Agent, or Firm* — KDW Firm PLLC

(57) ABSTRACT

Certain aspects of the present disclosure provide a method for assessing the performance of a physical activity, including: recording motion capture data while a training subject demonstrates a physical activity sequence; identifying one or more primary body elements based on the motion capture data; deriving one or more path characteristic metrics based on a state variable set and the one or more primary body elements, wherein the state variable set defines the state of a body at any given time; and defining an ideal activity path of the physical activity sequence based on the one or more path characteristic metrics.

20 Claims, 13 Drawing Sheets

Related U.S. Application Data

(60) Provisional application No. 62/851,009, filed on May 21, 2019.

(51) Int. Cl.
| | | |
|---|---|---|
| *G06T 7/20* | (2017.01) | |
| *G06T 7/70* | (2017.01) | |
| *G06V 40/20* | (2022.01) | |
| *G06F 18/22* | (2023.01) | |
| *G06V 10/74* | (2022.01) | |
| *G06V 40/10* | (2022.01) | |

(56) References Cited

U.S. PATENT DOCUMENTS

| | | |
|---|---|---|
| 9,773,330 B1 | 9/2017 | Douglas et al. |
| 9,781,494 B1 | 10/2017 | Barakat et al. |
| 9,987,520 B2 | 6/2018 | Shavit et al. |
| 10,186,041 B2 | 1/2019 | Chang et al. |
| 10,352,962 B2 | 7/2019 | Douglas et al. |
| 10,420,982 B2 | 9/2019 | Aragones et al. |
| 10,664,690 B2 | 5/2020 | Holohan |
| 10,923,224 B2 | 2/2021 | Sasaki |
| 11,182,599 B2 | 11/2021 | Takeichi et al. |
| 2005/0196737 A1 | 9/2005 | Mann |
| 2012/0190505 A1 | 7/2012 | Shavit et al. |
| 2015/0005910 A1 | 1/2015 | Ishii et al. |
| 2016/0307335 A1 | 10/2016 | Perry et al. |
| 2017/0103672 A1* | 4/2017 | Dey .................. G06F 3/011 |
| 2017/0169297 A1 | 6/2017 | Bernal et al. |
| 2017/0281054 A1 | 10/2017 | Stever et al. |
| 2018/0188284 A1 | 7/2018 | Douglas et al. |
| 2018/0189989 A1 | 7/2018 | Douglas et al. |
| 2019/0091515 A1 | 3/2019 | Shavit et al. |
| 2019/0336825 A1 | 11/2019 | Douglas et al. |
| 2020/0160044 A1 | 5/2020 | Sur et al. |
| 2020/0222757 A1 | 7/2020 | Yang et al. |

FOREIGN PATENT DOCUMENTS

| | | |
|---|---|---|
| CA | 3048678 A1 | 7/2018 |
| CN | 1933880 A | 3/2007 |
| CN | 11028415 | 9/2019 |
| EP | 1722872 A1 | 11/2006 |
| EP | 3563290 A1 | 11/2019 |
| JP | 2007520282 A | 7/2007 |
| JP | 2017207456 A | 11/2017 |
| KR | 100349338 B1 | 8/2002 |
| KR | 20070032628 A | 3/2007 |
| KR | 20160076488 A | 6/2016 |
| WO | 2005072831 A1 | 8/2005 |
| WO | 2018125741 A1 | 7/2018 |
| WO | 2019038452 A1 | 2/2019 |
| WO | WO2019/082376 A1 | 5/2019 |

OTHER PUBLICATIONS

International Preliminary Report on Patentability for the International Patent Application No. PCT/US2020/034096, dated Nov. 23, 2021, 5 pages.

* cited by examiner

SCORING METRIC FOR PHYSICAL ACTIVITY PERFORMANCE AND TRACKING

CROSS-REFERENCE TO RELATED APPLICATIONS

This application claims priority to pending U.S. patent application Ser. No. 16/880,693, filed May 21, 2020, which claims the benefit of U.S. Provisional Patent Application No. 62/851,009, filed on May 21, 2019, the entire contents of each application is incorporated herein by reference.

INTRODUCTION

Aspects of the present disclosure relate to systems and methods for quantifying and monitoring physical activities based on motion data, and in particular, to quantitatively assessing the performance of a physical activity given subject motion capture data provided by a motion capture system.

In a physical rehabilitation setting, patients are often prescribed physical therapies, which may include specific, physical activities, such as exercises targeting specific movements of specific limbs and joints. Typically, a patient is given written instructions for when and how to perform the physical activities (e.g., a certain number of repetitions of a specific exercise every twelve hours). Historically, patients have also needed to go to a physical therapy clinic, or to have a clinician visit them at home, to monitor their physical therapy and to get feedback and coaching to maximize compliance with their physical therapy. Such on-site monitoring generally improves the efficacy of the physical therapy, for example, by ensuring that it is performed correctly and consistently. However, this conventional practice is time-consuming, expensive, and logistically challenging. Moreover in-clinic or in-home physical therapy coaching may not be available to those with limited mobility or means. While patients can perform prescribed physical therapies on their own without professional support, there is no guarantee that the patients will follow instructions and use proper form—which is critical to the efficacy of the prescribed physical therapies. In fact, unsupported physical therapy frequently leads to inferior patient outcomes, higher chances of re-injury, and the like.

Notably, the same issues faced in the physical therapy context are present in other contexts, such as physical fitness training for performance improvement rather than injury recovery, in coaching of athletes for various sports, and in any other context where the consistency and quality of body motions may improve a desired outcome.

Accordingly, what are needed are systems and methods for quantitatively assessing the performance of a physical activity based on motion capture data.

BRIEF SUMMARY

Certain aspects provide a method for assessing the performance of a physical activity, including: recording motion capture data while a training subject demonstrates a physical activity sequence; identifying one or more primary body elements based on the motion capture data; deriving one or more path characteristic metrics based on a state variable set and the one or more primary body elements, wherein the state variable set defines the state of a body at any given time; and defining an ideal activity path of the physical activity sequence based on the one or more path characteristic metrics.

Other aspects provide processing systems configured to perform the aforementioned methods as well as those described herein; non-transitory, computer-readable media comprising instructions that, when executed by one or more processors of a processing system, cause the processing system to perform the aforementioned methods as well as those described herein; a computer program product embodied on a computer readable storage medium comprising code for performing the aforementioned methods as well as those further described herein; and a processing system comprising means for performing the aforementioned methods as well as those further described herein.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Aspects of the present disclosure provide apparatuses, methods, processing systems, and computer readable mediums for quantitatively assessing the performance of a physical activity based on motion capture data.

Overview of Physical Activity Tracking

Figure 1:
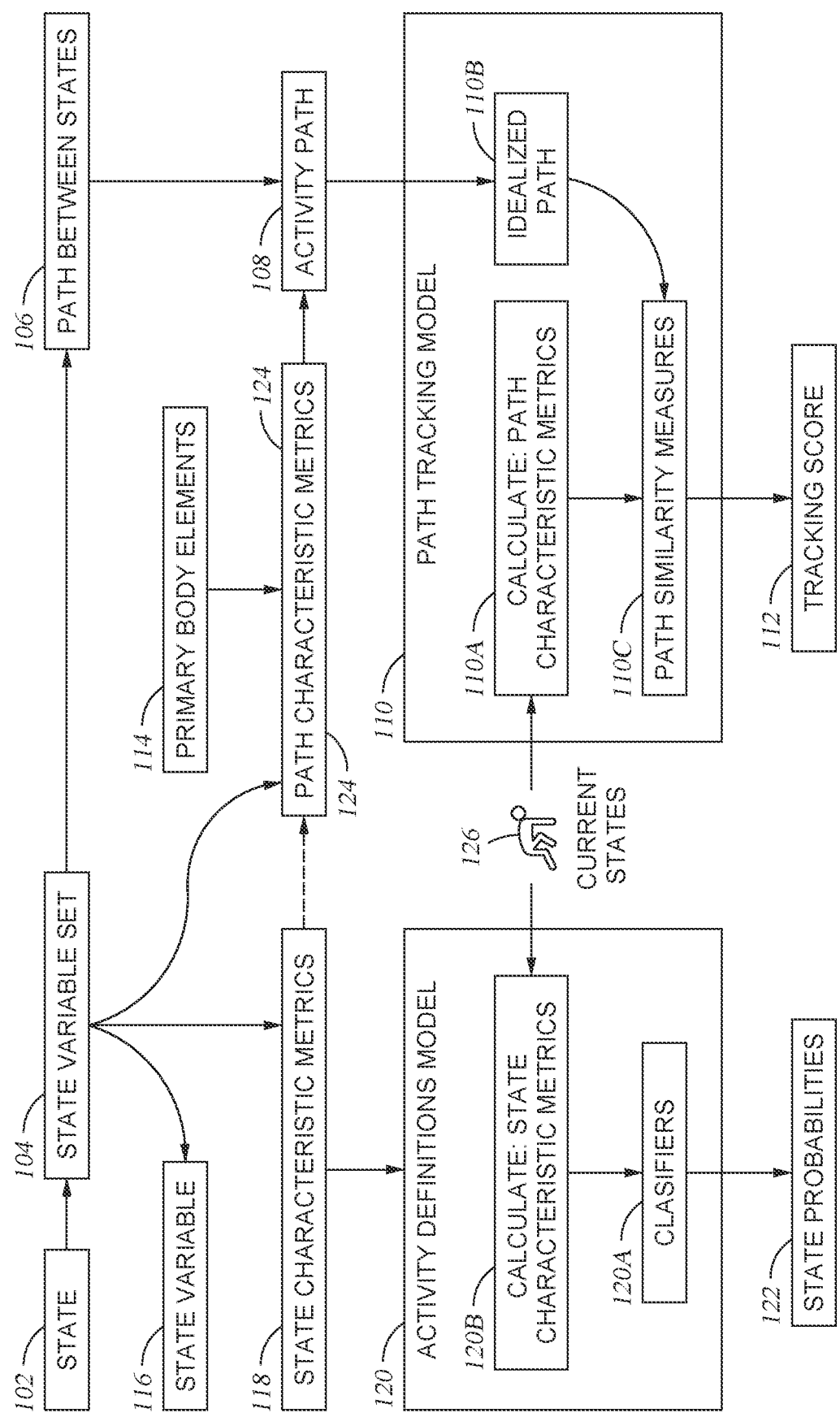
FIG. 1 depicts an example relationship diagram depicting various aspects that are described herein.

FIG. 1 depicts an example diagram depicting various aspects of a physical activity tracking and assessment system, as described herein.

Generally, a physical activity (or activity sequence) is a bodily activity that includes a temporal sequence of states (e.g., 102 or 126) of a subject's body. Physical activities may take many different forms. For example, a physical activity may comprise an exercise or other prescribed motion performed or practiced in order to develop, improve, or display a physical capability or skill.

A state (or activity state) 102 associated with a physical activity may generally include a particular position, pose, or bearing of a subject's body, whether characteristic or assumed for a special purpose. One or more states in a sequence of states defining a physical activity may be considered key states, and key states may be used to define a mathematical representation of a physical activity.

For example, the physical activity of sitting down may have a first key state of standing and a second key state of sitting. The states in between standing and sitting may not be considered "key" because they may not be important to defining the overall physical activity of sitting. However, as described in further detail below, a path between states (e.g., 106), including between key states, may be used by a path tracking model to quantitatively assess the performance of a physical activity defined by its key states.

Key states may be determined by experts, such as trainers, clinicians, doctors, or the like, or determined numerically based on analyses of temporal sequences of motion data associated with a physical activity. For example, points of inflection in a motion path of a particular body segment or joint may indicate a key state of a particular physical activity.

In some cases, a physical activity may be further defined by temporal specifications, such moving from one state to another state within a specified time, or holding one state for a specified time, to name just a few examples.

Each state in a physical activity state sequence may be defined with reference to individual segments or portions of a subject's body, such as the subject's head, neck, torso, arms, hands, fingers, legs, feet, bones, and others. States within physical activity sequences may be further defined by joints, which are generally connection points between two adjoining body segments that allow for some articulation of one segment in relation to another connected segment. In some cases, the individual segments and joints associated with a subject may be combined to form a mathematical body representation, such as a skeleton representation, or other more featured representations, such as an avatar.

A state (e.g., 102) may be programmatically described and tracked using one or more state variables 116 (e.g., in a set of state variables 104), which may include numeric and/or non-numeric variables. For example, a set of state variables may describe the position and orientation of limbs and joints relative to the body or an independent frame of reference, such as a coordinate system. In some cases, a set of state variables (e.g., 116) may fully define the state of a subject's body.

In addition to defining states, paths between states (e.g., motion paths or state transition paths) may also be defined. Generally a path between states (e.g., 106) may be expressed as an ordered sequence of state variable sets, where each state variable set may be derived from a full state variable set (e.g., 104), used for tracking transitions between and including any two discrete states. For example, a path may include a series of states (e.g., poses), typically ordered by a time or sequence in which they are performed. Because each state may be described by a state variable set (e.g., 104 in FIG. 1), a path may be described as a sequence (or series) of these state variable sets. In some embodiments, the sequence may be ordered using temporal values or the order may be specified otherwise. A path between states may also be expressed as a mathematical function.

Generally, an activity path between states may be multi-dimensional, such as an n-dimensional path between discrete states. The dimensionality may depend on, for example, the number of body primary elements associated with the activity and the reference frame in which they are expressed. In such cases, each dimension of the path between states may be considered a path component. In some cases, a path between states may be projected to a lower dimensionality, such as a three-dimensional path projected to a two-dimensional plane.

For example, an activity path based on a single joint (a type of body element), may include an ordered series (e.g., in time) of three spatial dimension values for that primary body element as it moves through the activity path, and thus be three-dimensional. As another example, an activity path based on a single limb (another type of body element) may include an ordered series of six spatial dimension values, where three spatial dimension values are associated with a first end of the limb (e.g., at a first joint) and the other three spatial dimension values are associated with a second end of a limb (e.g., at a second joint). As yet another example, a body element may be represented by three spatial dimensions at a first joint location and a number of orientation references (e.g., in Euler angles). As a further example, an activity path based on a plurality of primary body elements may include an ordered series of spatial dimension values for each primary body element in the plurality as it moves through the activity path. Notably, an activity path may be based on any number of body elements and thus any number of spatial, orientation, and other non-spatial dimensions, such as temporal dimensions, and others.

Physical activity state sequences may be captured and digitized through a process of motion capture, motion monitoring, motion tracking, or the like, which all generally refer to a process for generating data regarding a subject's kinematic motion and static poses using a variety of electronic sensors. Generally, a motion tracking system may include hardware and software components configured to monitor a subject's physical activity (e.g., movements, exercises, etc.). In some embodiments, a motion capture device may include optical camera systems with image processing, marker based tracking systems with various marker (active, passive, semi-passive, modulated) and detector (optical, radio frequency) types, depth camera systems with object recognition algorithms, inertial measurement units, mechanical exoskeleton motion capture systems, or magnetic flux measurement systems, to name a few. One example of a motion tracking system is the KINECT® sensor and its associated pose detection software by MICROSOFT®.

States in a physical activity state sequence may be compared to generate state differentiation variables. For example, a plurality of candidate inter-state differentiation variables may be defined based on body segments and joints in order to identify or improve identification of differences between states, including key states, of a physical activity. In some embodiments, the plurality of candidate inter-state differentiation variables may be tested to determine a subset of inter-state differentiation variables that are most effective for identifying particular states, such as key states, in captured motion data. The selected subset inter-state differentiation variables may be referred to as state characteristic metrics (e.g., 118), which are generally used by a physical activity definition model (e.g., 120) for identification and tracking of key states of a physical activity in motion data.

An ideal physical activity sequence may be defined, for example, by capturing motion data of a professional performing a physical activity in a prescribed manner and thereafter defining key states of the physical activity based on the captured motion data. As above, the key states may be defined manually, such as by a professional, or automatically, by analyzing the change in variables in captured motion data during performance of the ideal physical activity sequence. Further, in some implementations, key states can be numerically defined without a sample of collected motion capture data, such as by use of a skeletal data model.

Once a physical activity has been defined (e.g., by way of quantified state characteristic metrics), a physical activity definition model (e.g., 120) may be generated to determine (e.g., recognize or identify) states, such as key states, of the physical activity in captured motion data. Further, the physical activity definition model may compare the determined states with states of an ideal physical activity state sequence to "score" a subject's performance of the physical activity and/or to provide live feedback to the subject on the quality of the performance of the physical activity. This enables, in effect, live monitoring and feedback to a subject without the need for an on-site professional.

In some embodiments, a physical activity definition model (or physical activity model) (e.g., 120) comprises one or more classifiers (e.g., 120A) that are configured to determine probabilities (e.g., 122) that a particular state is represented in captured motion data. Further, for each classifier of the physical activity model, a classifier confidence may be determined as a quantitative assessment corresponding to the classifier's performance in determining a correct state, classification, or category of captured motion data. Determination of particular states via the physical activity definition model may further lead to determination that a defined physical activity, which comprises some or all of the determined states, is represented in the captured motion data.

The combination of classifiers (e.g., 120A) and state characteristic metrics (e.g., 120B) enables a single physical activity definition model to generate predictions regarding a plurality of defined states and physical activities in captured motion data.

In addition to determining states with an activity definition model (e.g., 120), the performance of a physical activity may further by quantitatively assessed based on paths of body segments and joints between states in the physical activity.

Figure 3:
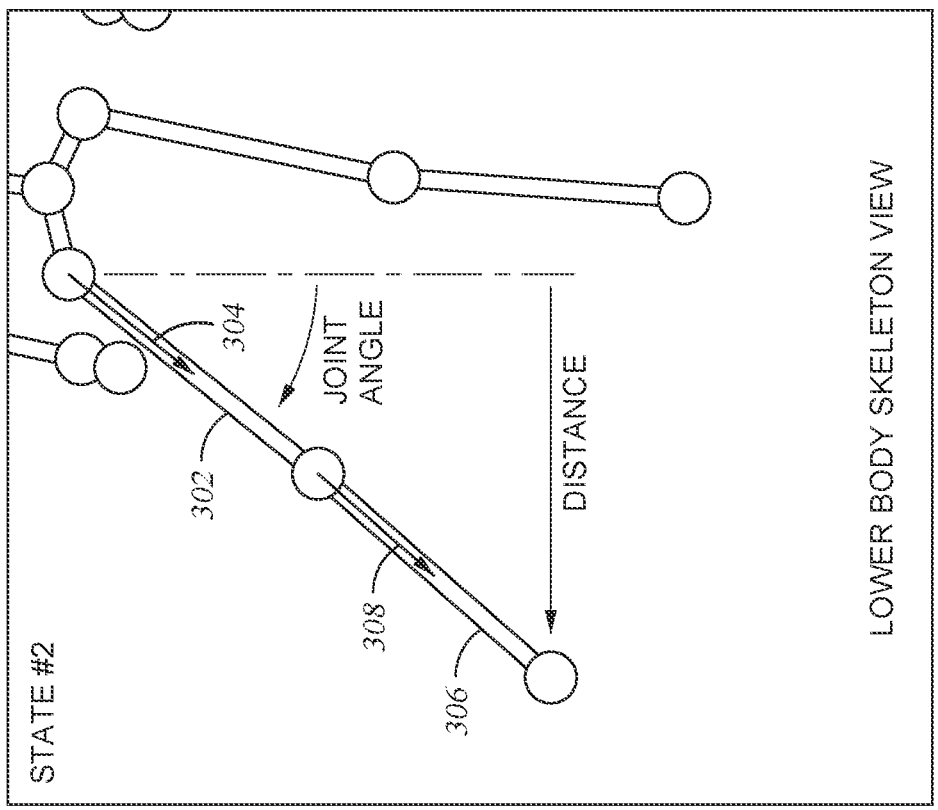
FIG. 3 depicts an example of skeletonization output from a motion capture source with primary body elements identified.
Figure 3:
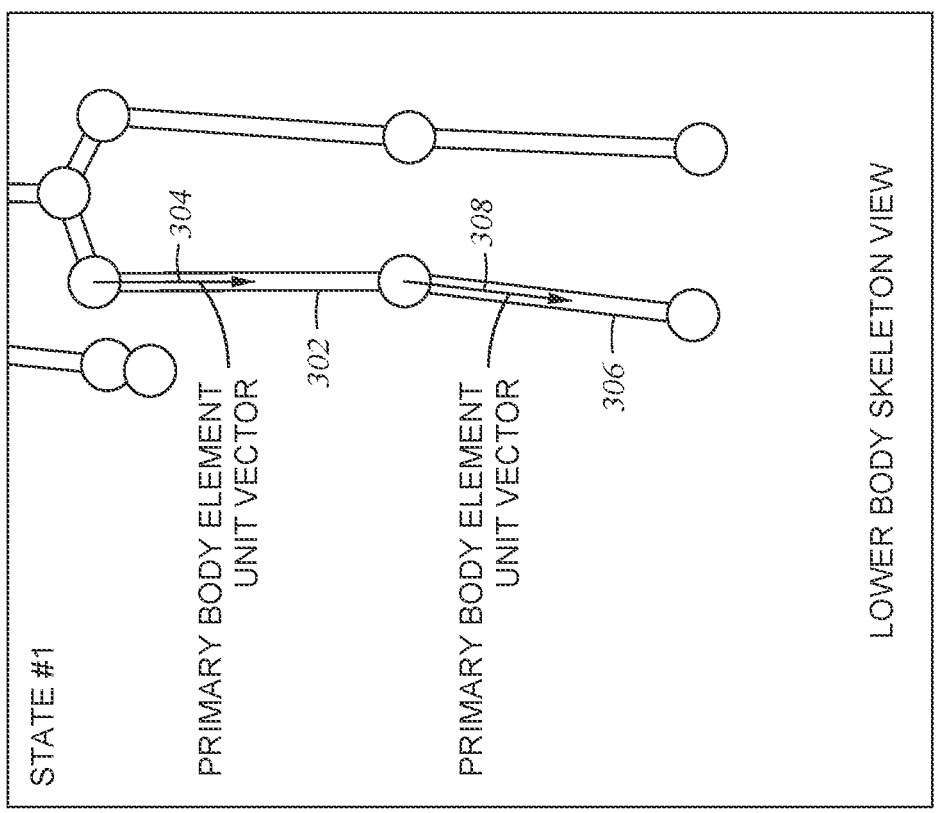

In some cases, the motion paths of body segments may be based on selected primary body elements (e.g., 114), which are generally elements of a subject's body usable for defining, tracking, and assessing activity form and/or performance. FIG. 3, described in more detail below, depicts an example of primary body elements in transition between two states in a physical activity sequence.

Primary body elements may be representative of the path between states. For example, the transition from a first state to a second state may involve significant motion of a subject's legs relative to its torso, but not its head and neck relative to its torso. Thus, the legs may be considered primary body elements in such a scenario. In some embodiments, a primary body element may be associated with one or more state variables (e.g., 116).

In some cases, primary body elements may be identified directly by an expert practitioner. Beneficially, during path tracking model formulation, the expert may refine a list of path characteristic metrics associated with primary body elements in order to place more emphasis on tracking body elements of greater interest.

In other embodiments, the primary body elements may be determined algorithmically. For example, primary body elements may be determined numerically from analysis of state variables (e.g., 104) between states (e.g., key states) in a physical activity sequence. For example, a numerical approach may be based on the mechanical work performed by each body element as a subject moves through an activity sequence. Analyzing the quantified work performed may inform identification of primary body elements for that physical activity sequence, or portion thereof.

A path characteristic metric (e.g., 124) is generally a state variable associated with or derived from one or more primary body elements used to define significant components of an activity sequence.

Path characteristic metrics may be used to define activity paths (e.g., 108). For example, an activity path or trajectory (e.g., 108) may generally be represented by one or more path characteristic metrics (e.g., a set of path characteristic metrics) for each intermediate state (transition region) between and including an activity path's beginning key state and ending key state.

An ideal activity path (e.g., 110B) is generally a desired activity path (e.g., as defined by an expert) associated with the full or partial course of a physical activity sequence.

A path similarity measure (e.g., 110C) is generally a numeric value which quantifies the similarity between actual activity paths (or trajectories) and an ideal activity path (e.g., 110B).

A path tracking model (e.g., 110) may generally include one or more path similarity measures (e.g., 110C) used to assess the complete motion in a physical activity sequence as compared to an ideal activity path (e.g., 110B). The path tracking model may generate path tracking scores (e.g., 112), which are generally values assessing a subject's performance of an activity path when compared to an idealized activity path.

Assessing Performance of a Physical Activity With a Path Tracking Model

Figure 2:
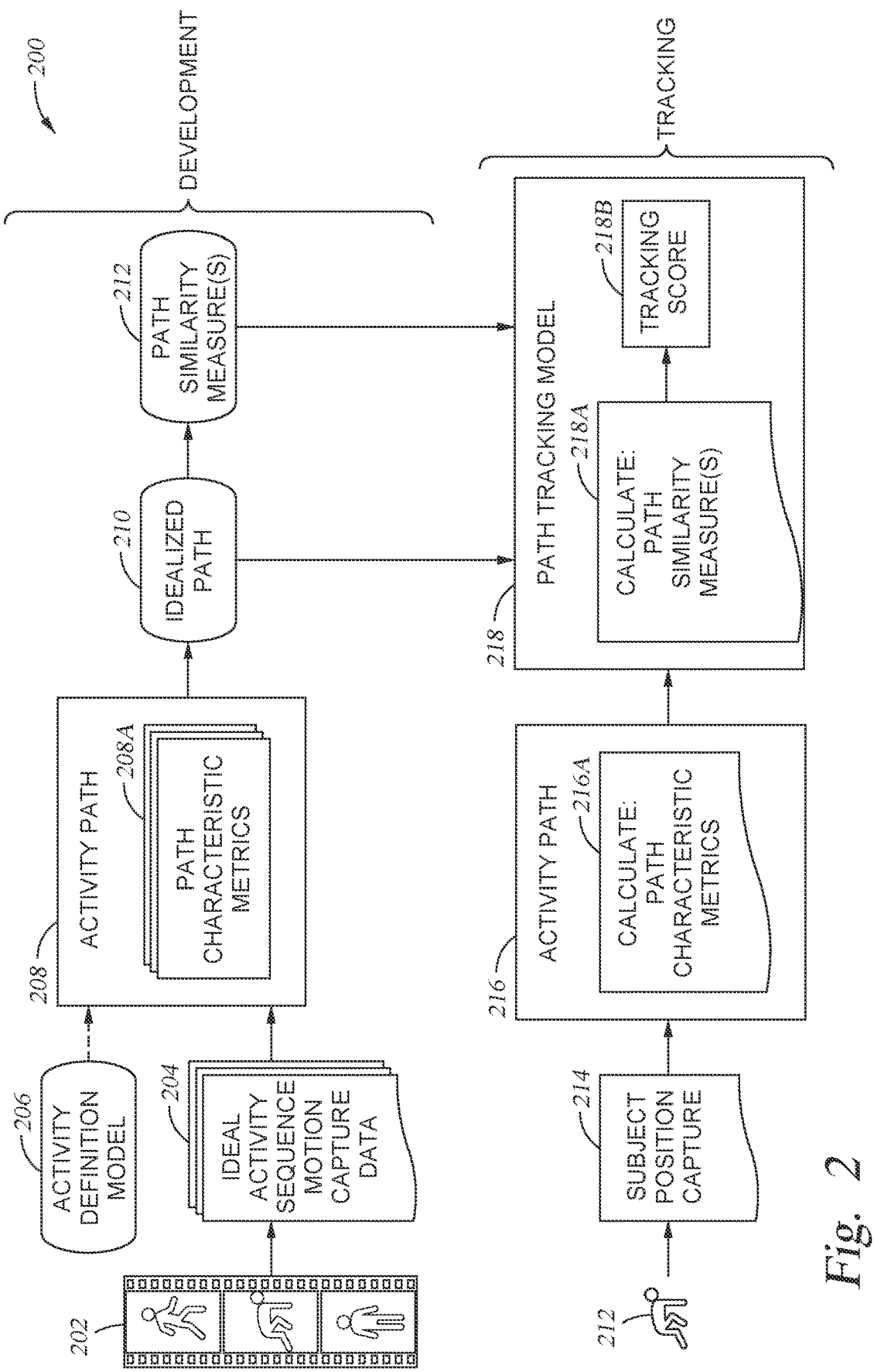
FIG. 2 depicts an example process for developing and implementing a path tracking model.

FIG. 2 depicts an example process for developing and implementing a path tracking model, such as 110 described above with respect to FIG. 1.

A path tracking model may be developed for use in assessing a subject's performance of a physical activity sequence, or a portion thereof. Development may generally begin with capturing motion data (e.g., using a motion capture system) while a training subject (e.g., an expert) demonstrates a specific ideal activity sequence, such as at 202 and 204. Analysis of the captured motion data, including the movement of various body elements within an activity path between key states of the activity sequence, enables identification of primary body elements that are useful for monitoring activity form, progression, and completion.

Recording the activity sequence (e.g., at 204) may be performed for example by a system comprising a computer accessing a motion capture device and running software algorithms that process the data from the device. Such a system may provide motion capture data for an activity by observing a trainer (e.g., an expert practitioner, possibly a clinician like a physiotherapist) enacting the activity.

A motion capture device may include optical camera systems with image processing, marker-based tracking systems with various marker (active, passive, semi-passive, modulated) and detector (optical, radio frequency) types, depth camera systems with object recognition algorithms, inertial measurement units, mechanical exoskeleton motion capture systems, or magnetic flux measurement systems, to name a few examples.

From recorded motion capture data, the training subject's state and activity progression may be quantified by extracting the coordinates of the primary joint positions of the trainer subject during the physical activity sequence. The training subject's body elements and limbs can then be determined to create a skeleton reconstruction based on the data captured by the motion capture system. Generally, each body element may be defined by a length between distinguishing joints and a unit vector giving its orientation in a given coordinate frame. A unit vector has a length of one and can be used to represent spatial direction/orientation in a given coordinate space.

Beneficially, implementing a unit vector-based approach for quantifying activity paths may be more robust than using Euclidean distance measures to track subject movement. For example, calculating body element unit vectors is a normalization process that may provide better tracking capabilities for subjects of varying biometrics.

Joint angles may also be calculated using vector operations on adjoining body element vectors.

Determining an Activity Path

An activity path is generally a motion path followed by a body element (e.g., a leg, an arm, a torso, etc.) while performing a physical activity sequence. For example, during a push-up, a subject's torso may move through a path that goes down initially and back up again. In some cases, activity paths may be defined with reference to key states of a physical activity sequence, such as the starting with a first key state and ending at a second key state.

An activity path may be quantitatively defined based on identification of one or more path characteristic metrics (e.g., 208A) that characterize the activity path. In some embodiments, a path characteristic metric may include a temporal aspect, such as an amount of time taken to complete the activity path.

In some embodiments, path characteristic metrics may be directly derived from state characteristic metrics (e.g., 118 in FIG. 1) used in an activity definition model (e.g., 206). For example, in one embodiment, classifiers within activity definition model 206 may be used to track path characteristic metrics 208A. Thus, in some embodiments, path characteristic metrics may be associated with and/or defined by the state characteristic metrics associated with the classifiers.

As another example, path characteristic metrics 208A may be directly identified by a clinician, doctor, physical therapist, or the like based on observation of a physical activity sequence and professional assessment.

In some embodiments, path characteristic metrics 208A may be based on one or more primary body elements. As above, primary body elements are generally components of a subject's body that undergo significant motion and/or represent the majority of the mechanical work done by a subject in performing a physical activity sequence, or some portion thereof.

The path characteristic metrics (e.g., 208A) may then be used to quantitatively define an ideal activity path 210 as well as to track variations from the ideal activity path. The ideal activity path 210 for a physical activity sequence may incorporate one or more of the path characteristic metrics 208A.

Determining an Ideal Activity Path

An ideal activity path (e.g., 210) may be determined and compared to a subject's actual activity path to assess the performance of the subject in completing a physical activity sequence, or some part thereof. In some embodiments, ideal activity path 210 includes spatial and/or temporal information regarding how a subject should perform a physical activity sequence, or a portion thereof.

Ideal activity path generation may start by first collecting ideal physical activity sequence motion data, such as at 204. The captured motion data may be used to define ideal activity path 210, which may include a quantification of the motion of one or more primary body elements throughout the physical activity sequence, or some portion thereof. As above, the physical activity sequence may be performed by experts demonstrating the ideal physical activity while motion data is captured.

Figure 5:
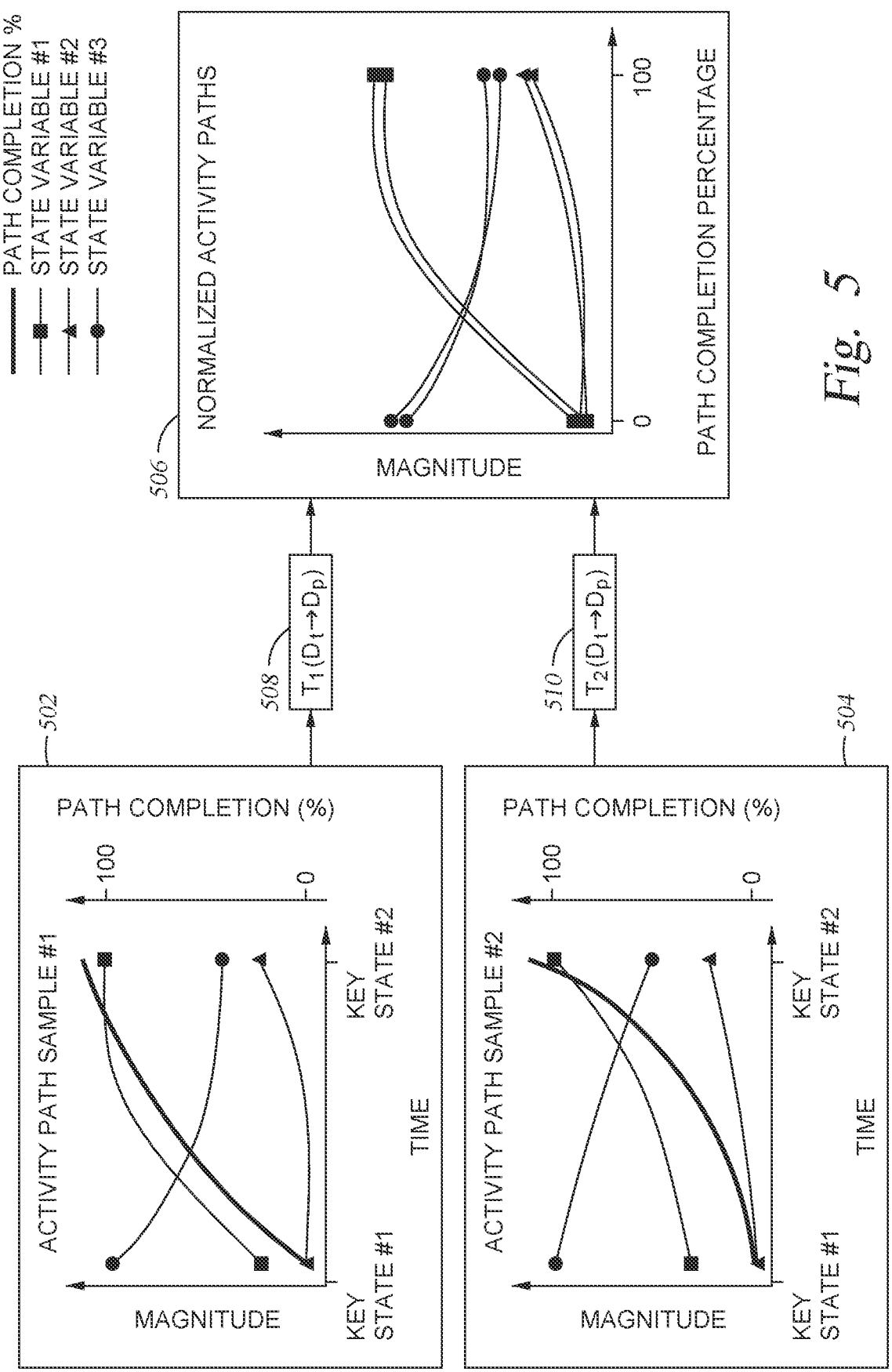
FIG. 5 depicts an example of activity path normalization.
Figure 6:
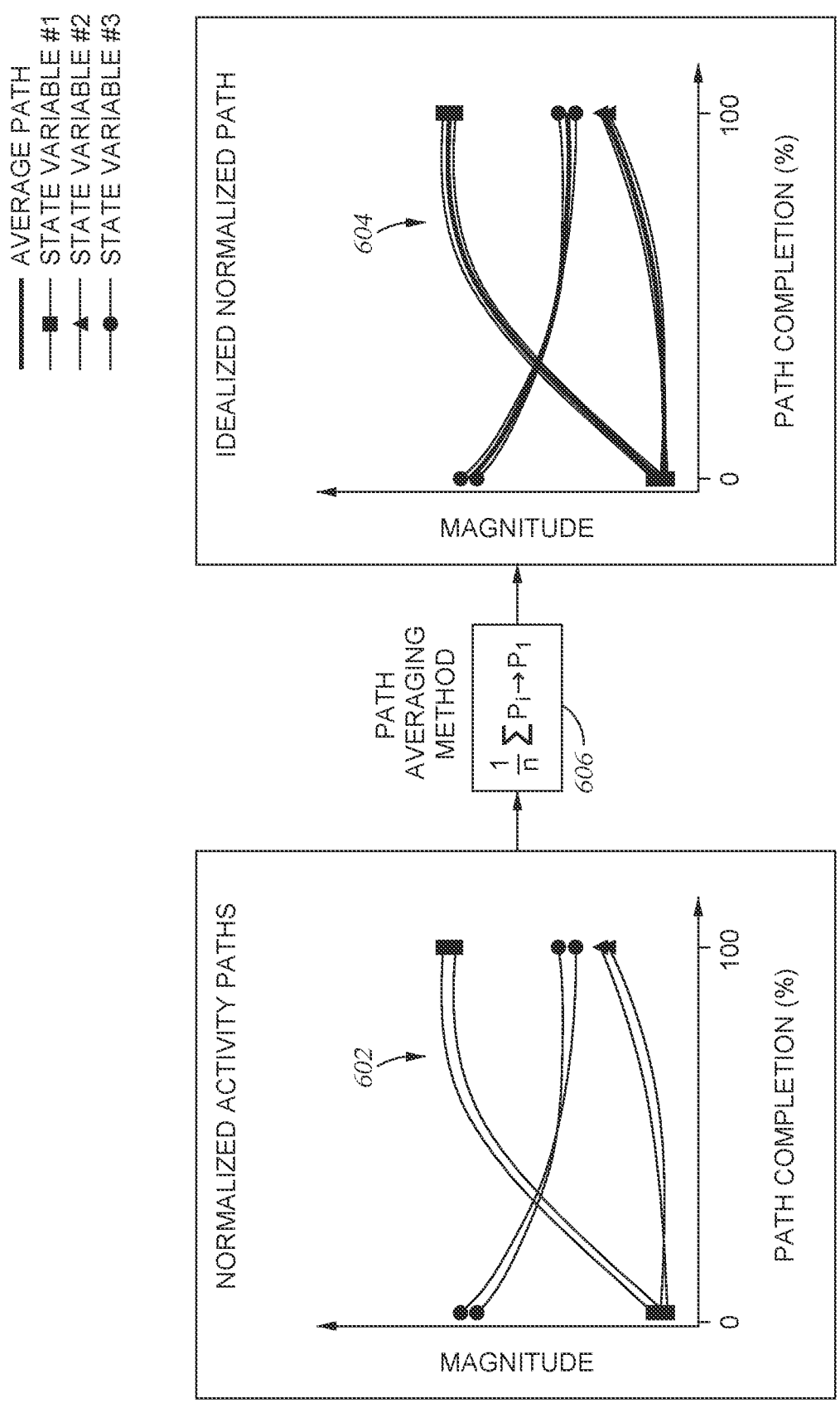
FIG. 6 depicts an example method of utilizing averaging to combine several normalized activity path samples into one mean normalized path.

In some embodiments, an ideal activity path may be based on the collection of several sample data sets of captured motion data from ideally performed activity sequence repetitions, such as by an expert. FIGS. 5 and 6, described in more below, demonstrates one example process determining an ideal activity path based on a plurality of activity path samples data sets.

In certain situations, it may be advantageous to capture motion data from multiple subjects and/or multiple tracking methodologies or devices. Differences can be found in joint positions and body element orientation for training subjects of varying size and shape depending on the motion capture platform used. This provides activity paths with wider ranges of acceptable orientations and will result in more robust tracking performance for varying subjects. It should be noted that there are situations where the requirement may be to customize the activity for specific user(s) or devices in which case the idealized path formulation can be restricted to those specific configurations.

Path similarity measures 212, which quantify the similarity between paths, may be determined based on ideal activity path 210 and path characteristic metrics 216A.

Beneficially, ideal path determination may be an automated and trainable process capable of using data from varying subjects. This feature may result in more robust and tunable tracking capabilities.

Configuration of Path Tracking Model

Tracking and assessing a subject's physical activity sequence performance is improved by comparing the subject's activity path 216 to ideal activity path 210. In some embodiments, a path tracking model (e.g., 218) containing one or more path similarity measure (e.g., 218A), may track a subject's motion throughout an activity and may provide a tracking score (e.g., 218B) for overall assessment. Tracking score 218B generally provides an objective metric to assess the similarity between the subject's activity path (e.g., captured in motion data at 214) and the ideal activity path (e.g., 210).

Beneficially, tracking score outputs from a path tracking model (e.g., 218) provide users with additional information regarding their performance over the complete course of an activity path. This scoring information can be utilized as additional feedback to aid subject training and may facilitate corrective actions with the intent to better demonstrate the proper technique desired by, for example, a prescribing clinician.

In some embodiments, the subject's activity path 216 includes path characteristic metrics (e.g., 216A), which define the significant components of the subject's motion throughout the course of a physical activity sequence, or portion thereof. Path tracking model 218 monitors these path characteristic metrics in order to assess a subject's performance of a physical activity sequence. For example, path tracking model 218 may compare the subject's path characteristic metrics (derived from the captured motion data at 214) to ideal activity path 210 to determine path similarity measures 218A.

In some embodiments, ideal activity path 210 is segmented based on key states occurring during performance of the physical activity sequence. In such cases, different path characteristic metrics 216A may be used for each segment of the segmented ideal activity path.

In some embodiments, path similarity measures may include, for example, root mean square deviation, Minkowski distance, Frechet distance, Hausdorff distance, Mahalanobis distance, Cosine distance, radial basis function kernels, and others. More generally, a path similarity measure can be any measure capable of numerically comparing the difference between activity paths. Advantageously, many types of path similarity measures may be used and configured to suit a specific end task requirement without any structural changes to the methods described herein. For example, if the timing of a physical activity sequence is an important feature, a measure with a temporal component can be implemented to provide additional feedback.

In some embodiments, tracking score 218B may be a based on a plurality of path similarity measures 218A. The process of combining one or more path similarity measure 218A into a composite tracking score 218B may be configured, for example, to place greater emphasis on certain primary body elements or on certain motion characteristics (temporal vs. spatial), to name a few examples.

Path tracking model 218 may be further configured to provide tracking score feedback at various phases of a physical activity sequence, or at different frequencies during a physical activity sequence. In some implementations, continuous tracking scores may be output in real-time during capture of a subject's motion (e.g., at 214). In other embodiments, tracking scores may be calculated at the end of each physical activity sequence, or portion thereof. For example, tracking scores may be provided at each key state in a physical activity sequence.

Use of Path Tracking Model to Monitor Subject Activity

Figure 8:
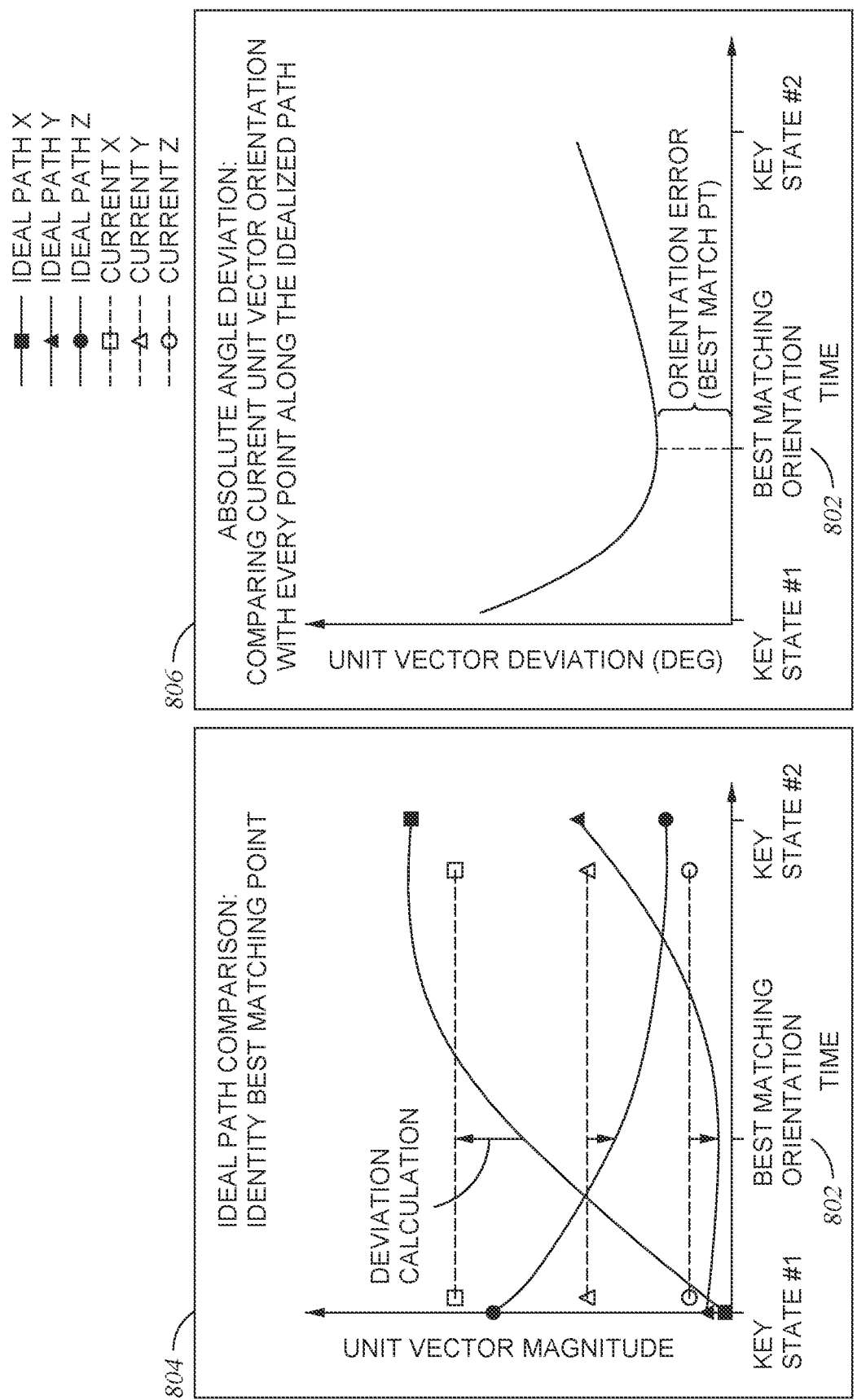
FIG. 8 depicts an example method for finding the best matching state along an ideal activity path based on a current orientation of a primary body element.

In some embodiments, a path similarity measure (e.g., 218A) of a path tracking model (e.g., 218) may be configured to analyze each point along an ideal activity path (e.g., 210). Because the subject's intended motion may not be known a priori, path tracking model 218 may determine the best matching ideal activity path based on the subject's performed path. FIG. 8, described in more detail below, describes one method of determining the best matching state along an ideal activity path.

As subject 212 transitions between key states of a physical activity sequence, its path characteristic metrics 216A are compared with ideal activity path 210 until the next key state in the activity sequence is achieved. During this transition between key states, the current path characteristic metric values may be compared to points along an ideal activity path in order to determine a best matching orientation/position. To this end, each point along an ideal activity path may be considered in ideal path state represented by a state variable set representing an ideal position and/or orientation for one or more body elements. Thus, captured motion data may be compared to each point along an ideal activity path (e.g., 210) so that an appropriate ideal activity path state may be determined based on subject 212's current state.

For example, when primary body element unit vectors are implemented as metrics (as described in more detail below with respect to FIGS. 3 and 4), the orientation difference between subject 212's current state and the best matching ideal activity path state may be expressed as an angular deviation of the primary body element(s) as compared to the ideal activity path.

The angular deviation between the body element's actual and ideal unit vectors may be calculated using, for example, a vector dot-product operation that is measured about the axis defined by the cross-product between the two vectors, according to:

$$\theta = \cos^{-1}(\vec{u} \cdot \vec{v}) \quad \text{(Eq 1)}$$

where $\theta$ is angular deviation, $\vec{u}$ is the actual unit vector orientation, and $\vec{v}$ is the ideal unit vector orientation. Equation 1 thus provides the absolute angle deviation between an ideal body element orientation and the actual orientation of the body element in the captured motion data.

These orientation differences may be recorded and stored as subject 212 moves between key states and may be used to calculate a spatial tracking score for feedback. In one embodiment, the tracking score i may be calculated according to:

$$\tau = \frac{1}{n} \sum_{k=1}^{n} |\theta_i| \quad \text{(Eq. 2)}$$

where $\theta_i$ is the angle deviation of sample i and n is the total number of samples along the path. Equation 2 takes the average of all angle-deviation samples recorded during the activity path and is thus an averaging equation that may be used to produce a tracking score (e.g., 218B) at the completion of an activity path.

The time durations of each key-state transition may also be compared to that of ideal activity path 210 to produce a temporal tracking score for an activity path. The temporal tracking score may be implemented into a path similarity measure to better track activity timing characteristics. Once again, the combination of path similarity measures can be configured to place greater emphasis on certain characteristics of an activity.

In some embodiments, tracking scores (e.g., 218B) may be provided to a subject (e.g., 212) in real time with little to no latency depending on the motion capture source and supporting computer hardware. This live tracking score feedback may be used as the basis of other metrics of interest, like the risk of injury to subject 212 based on the subject's deviation from the ideal activity path 210 during an activity sequence.

For example, as subject 212 deviates further from ideal activity path 210, tracking score 218B will reflect this increase. If tracking score 218B deviates beyond a threshold, then a cautionary warning may be provided to subject 212, which may beneficially result in a reduced risk of injury to subject 212.

Path tracking models may further be configured to produce a set of tracking scores, wherein each tracking score in the set of tracking scores is associated with a specific body element (e.g., an arm, a leg, etc.). Additional tracking scores may also be used to provide additional feedback to subject 212, such as by isolating problematic body regions and targeting specific areas of activity performance improvement.

Note that while the aforementioned example uses primary body element unit vectors as path characteristic metrics and segmented ideal activity paths based on key states of a physical activity sequence, this is just one example embodiment and other embodiments may be implemented differently.

Example Primary Body Elements

FIG. 3 depicts an example of skeletonization output of a subject's lower body portion from a motion capture source with primary body elements identified. In particular, FIG. 3 depicts primary body elements 302 and 306 in different orientations between two key states in an activity sequence. As above, primary body elements 302 and 306 may be identified by a clinician based on work performed by the patient during the activity sequence or by a numerical approach.

FIG. 3 further depicts an example of primary body element unit vectors 304 and 308, which may be used as path characteristic metrics (e.g., 216A in FIG. 2) in some embodiments. Notably, the methods described herein work with any quantitative representation of an activity path. In other words, it is not necessary that an activity path be represented only as a set of unit vector trajectories. Further, note that it is possible to derive a subject's joint positions using mathematical operations on captured motion data from tracking systems that do not directly provide joint positions.

Activity Paths Based on Primary Body Element Unit Vectors

Figure 4:
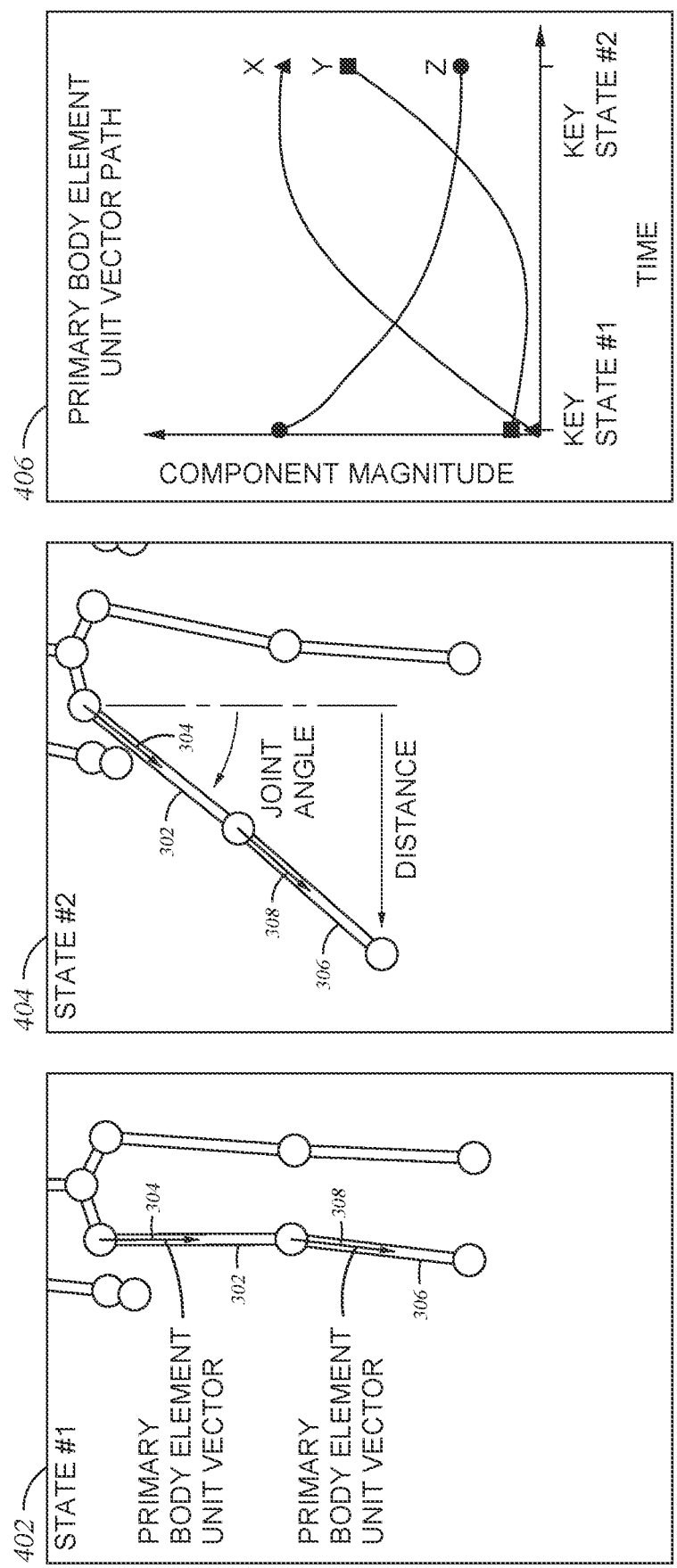
FIG. 4 depicts an example of using primary body element unit vectors to derive path characteristic metrics to measure a subject's physical activity path.

FIG. 4 depicts an example of using primary body element unit vectors to derive path characteristic metrics (e.g., 208A and 216A in FIG. 2) to measure a subject's physical activity path.

In particular, this example depicts the differences in unit vector orientations between two key states, 402 and 404, in an activity sequence by plotting magnitude differences for each of three component directions (X, Y, and Z) of the primary body element unit vector. Plot 406 depicts the values of the path characteristic metrics of the unit vector trajectory for a primary body element expressed as a function of time as the subject transitions from key state 402 to key state 404.

Activity Path Normalization

FIG. 5 depicts an example of activity path normalization. In particular, FIG. 5 depicts a path completion normalization approach in which a plurality of recorded activity path samples, 502 and 504, are normalized with respect to time by using the start and end points of the physical activity sequence, which in some cases may be key states. Once time-normalized, the activity paths may be expressed as a percentage of completion rather than in time, such as depicted in plot 506, via a transfer function, such as 508 and 510.

For example, transfer functions $T_1$ (508) and $T_2$ (510) transform the time-domain $D_t$ output of plots 502 and 504, respectively, into normalized domain $D_p$ output, as in plot 506.

In some embodiments, the normalization approach depicted in FIG. 5 may be used for ideal activity path determination, as described above with respect to FIG. 2.

Figure 7:
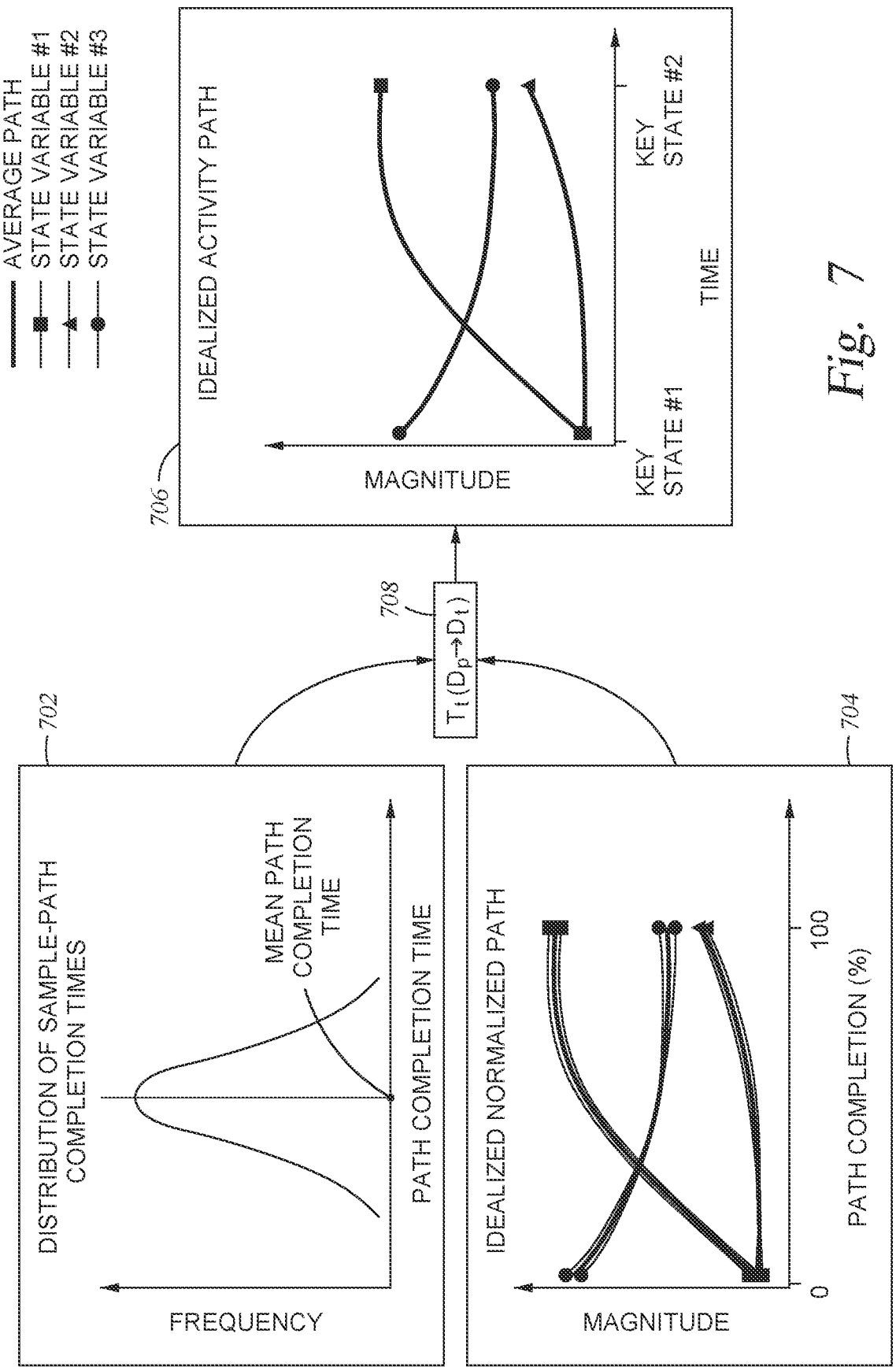
FIG. 7 depicts an example method of implementing the mean path completion time to convert the mean normalized path into an ideal activity path expressed as a function of time.

This normalization process allows for activities of varying rates to be compared on an equal scale. In this normalized domain, collections of normalized paths may be combined to calculate a mean path of the sample motion capture datasets, such as described with respect to FIG. 6. Further, a mean path trajectory may then be transformed back to the time domain using the mean path completion time observed in the training data, as shown in FIG. 7. Once transformed back into the time domain, a mean path represents the idealized path for that activity.

When normalizing activity paths, all similar path characteristic metrics of the normalized activity paths may be combined using an averaging method and converted back into a function of time using a mean observed time for path completion, such as depicted in FIG. 6. This process produces a mean path as a function of the normalized time, and also a standard deviation of the path over the normalized time, as depicted in FIG. 7. A standard deviation around the mean completion time may also be determined.

Activity path normalization may also be done in a piecewise fashion by segmenting and normalizing the activity path samples using each physical activity key state to mark the idealized path start and end point. As above, physical activities may be defined as a sequence of key states the subject must achieve over the course of a physical activity. Creating separate segments of an ideal activity path, delineated by each key state in the activity, may provide for a more precise normalization process, and may also facilitate tracking scores with more concentrated details regarding certain segments of the activity path. In this case, over the course of the full activity sequence, the idealized path would have a piecewise formulation for each transition region between activity key states. Each segment of the activity path may include both the starting and ending key-state, possibly creating some state overlap when combined into one complete activity path.

Normalization of activity path samples may also be done using an activity definition model (e.g., 120 in FIG. 1). Knowledge of path completion percentage information may be used to improve the synchronizing of sample activity paths before the calculation of an idealized activity path (e.g., 210 of FIG. 2). An activity definition model may be used to produce a measure of path completion percentage based on the classifier likelihoods produced comparing each transitional state along the path to the two key-states defining the activity path starting and ending points. This path completion percentage, defined as a function of time (or normalized time), allows for the creation of a transfer function T to convert the time-domain state variable data into a normalized domain based on path completion percentage. This implementation may help mitigate issues due to sample activity sequences being performed at varying rates.

In some embodiments, a normalization method may be implemented using primary body element orientations for activity path tracking, which may increase robustness to differences in subject biometrics and resulting skeletonization data. In particular, activity paths may be quantified and normalized by tracking the primary element unit vector orientation differences between the key states (as in FIG. 4).

For these primary body elements, tracking is performed by analyzing the unit vector orientation changes as the subject transitions from one key state to the other.

Calculation of body element unit vectors is a normalization process beneficially reduces the influence of variations in subject body type (height, weight, etc.). With the interest of tracking large numbers of subjects, with equal assessment, the use of unit vectors may be a more robust choice for use as path characteristic metrics.

In some embodiments, a combination of path similarity measures may also take into account the ideal activity path standard deviation observed during formulation of the ideal activity path.

Beneficially, a collection of activity path samples (e.g., 502 and 504) generated from captured motion data of ideally performed physical activity sequences may provide information regarding the acceptable limits of deviation from an idealized. In some embodiments, a mean path (idealized path), and the standard-deviation around this mean, can be calculated and may be accounted for in the path similarity measures.

Mean Normalized Path Determination

FIG. 6 depicts an example method of utilizing averaging to combine several normalized activity path samples 602 into one mean normalized path 604. In the depicted example, each common component (e.g., state variable) of the normalized activity path samples is averaged along the full path according to the following equation (606 in FIG. 6):

$$\frac{1}{n}\sum P_i \to P_1 \qquad \text{(Eq. 3)}$$

where n is the number of normalized path samples, $P_i$ is the ith normalized path sample, and $P_1$ is the normalized average path. Notably, this method can be used for producing an ideal activity path, such as a mean normalized ideal path.

Converting Mean Normalized Paths Into an Ideal Path

FIG. 7 depicts an example method of using a mean path completion time (as depicted in 702) to convert the idealized normalized activity path in plot 704 into an idealized activity path expressed as a function of time 706. In this example, transfer function $T_t$ (708) may be created using the mean path-completion-time to transform normalized domain $D_p$ output, as depicted in plots 702 and 704, into time-domain $D_t$ output, as depicted in plot 706.

Ideal Activity Path State Selection

As described above, a path tracking model can contain one or more path similarity measures (e.g., 218A in FIG. 2) that each produces a measure of similarity between an observed activity path (e.g., of a subject performing a physical activity sequence) and an ideal activity path. The output of the path similarity measures can be combined to produce one or more tracking scores providing an overall assessment of the activity performance. The combination of the path similarity measures can be performed in several acceptable methods and may be done to place greater emphasis on specific characteristics of the motion.

However, when tracking a subject's performance of a physical activity sequence, the path tracking model may need to determine an appropriate ideal activity path state to compare with the subject's observed activity path.

FIG. 8 depicts an example method for finding the best matching state along an ideal activity path based on a current orientation of a primary body element. In this example, the deviation from the current orientation is compared to every point along the ideal activity path, and an index at which the minimum orientation difference occurs is determined to be the best matching state along the ideal activity path.

In particular, during the progression of an activity path, components of a subject's observed state can be compared to an ideal activity path by a path tracking model as depicted in plot 804. Notably, FIG. 8 depicts an example of a spatial comparison independent of exercise timing or velocity. Rather, the example method identifies the best matching orientation 802 along the idealized path given the current orientation (in dimensions X, Y, and Z) of a primary body element. The deviation (or difference) of the current orientation is calculated (or compared) to every point along the idealized path, as shown in the plot 806. The index along the ideal activity path that shows the minimum orientation difference is determined to be the best matching point. This point along the idealized path shows the closest resemblance to the current state of the subject.

Throughout the progression of the subject's activity path, the minimum orientation difference for each motion capture data sample is determined. The calculated minimum deviation (e.g., point 802) may be provided as a tracking score for every sample of motion capture data during the progression of the path.

Further, once a subject completes a full motion of an activity path, and they are in the desired final key state, the collection of orientation differences may be analyzed to provide an aggregate tracking score based on the full collection of samples recorded through the entire activity path. Thus a tracking score may be generated at the completion of every activity path or designated path segment.

This minimum deviation approach is one on many acceptable methods of path tracking using a path similarity measure. The choice of other acceptable path similarity measures would facilitate slightly varying processes. For example, using a Frechet distance metric, the subject's observed activity path would be compared to the idealized path after the completion of the activity sequence. The Frechet distance would provide a measure of similarity between the paths taking into account the location and ordering of the samples along both paths.

Beneficially, the method of identifying a best-matching orientation along an ideal activity path, such as depicted with respect to FIG. 8, may provide a comparison which is time invariant, which allows for a more comprehensive analysis of activity motion differences (spatial vs. temporal).

Example Activity Path Tracking User Interface

Figure 9:
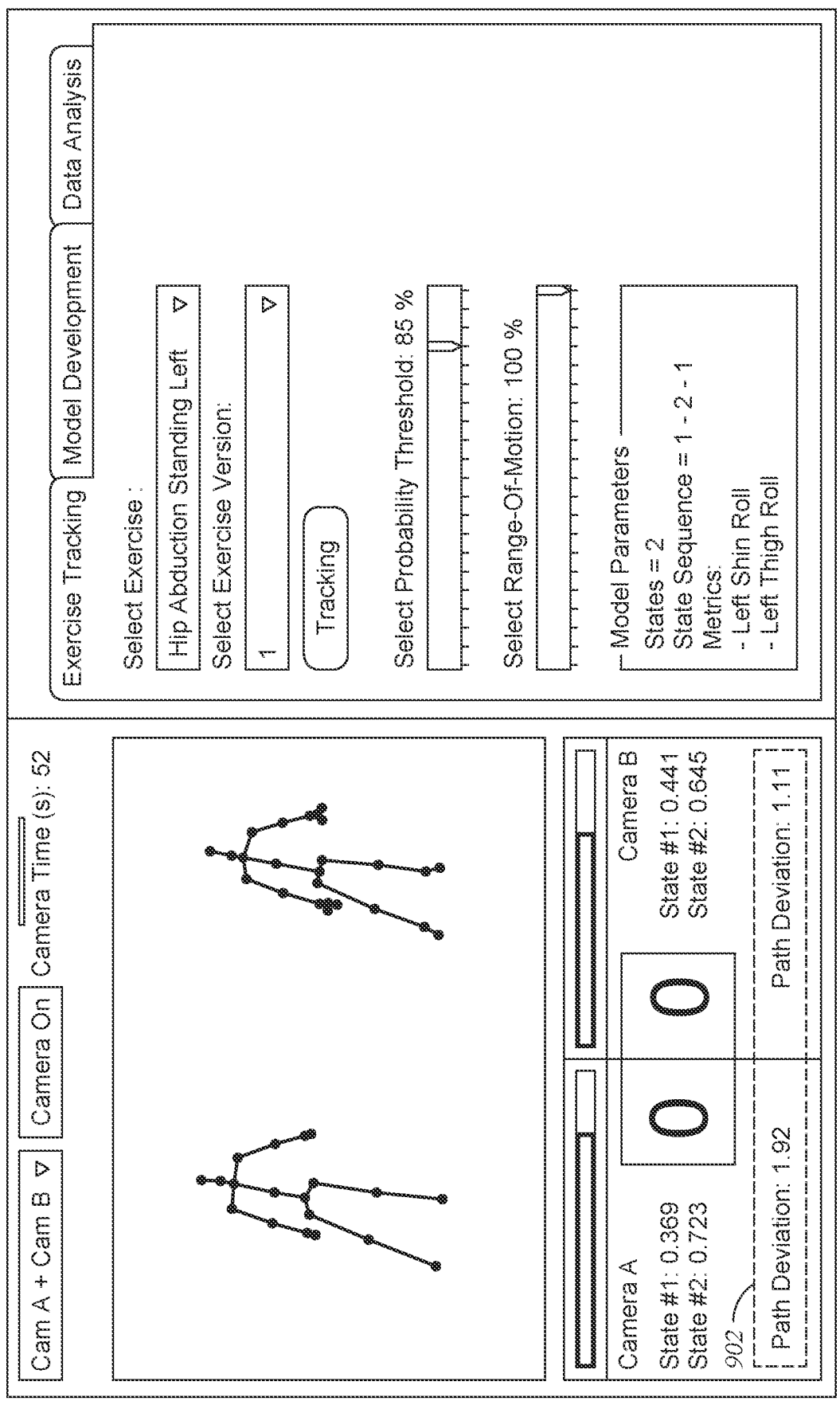
FIG. 9 depicts an example graphical user interface of a live activity path tracking application.

FIG. 9 depicts an example graphical user interface 900 of a live activity path tracking application. In this example, a subject is performing a standing left-leg hip abduction activity and transitioning between the two key states of the physical activity sequence.

Path deviation tracking scores 902 are displayed at the lower edge of the picture, such as may be calculated by a path tracking model (e.g., 218 of FIG. 2). In this case, the tracking score (path deviation) represents the minimum angle between the current orientation of the tracked one or more body elements and that of the closest matching state along the idealized path. Notably, each of the tracking scores in this example is based on a different motion capture source, such as two different motion capturing camera systems. Thus, multiple motion capture systems can be used concurrently.

Beneficially, the tracking score (e.g., 902) provided by the path tracking model may be used to provide a prediction of risk and allow for cautionary feedback to prevent potential injury during an activity. If the subject deviates greatly from the ideal path, live feedback from the path tracking model may reduce the risk of potential injury.

Alternative Approach Using Vector Algebra

FIG. 10 provides an example of an alternative approach for plotting and comparing activity paths using vector algebra.

Initially, each element of an activity path (e.g., 208 or 216 of FIG. 2) may be considered to be a vector of values each of which relates to or is derived from a set of state variables (for example, a vector of the path characteristic metrics). Each vector element of the activity path may be augmented with one or more time-based variables, which depict the temporal aspect of the activity. For example, a time augmentation could be the real time elapsed (in suitable units) since the beginning of the activity, or it could be the percentage of time elapsed relative to the time for the entire activity (or the activity between key states). An enhanced activity path may now be represented by a sequence of these augmented vectors, ordered temporally or otherwise.

Figure 10A:
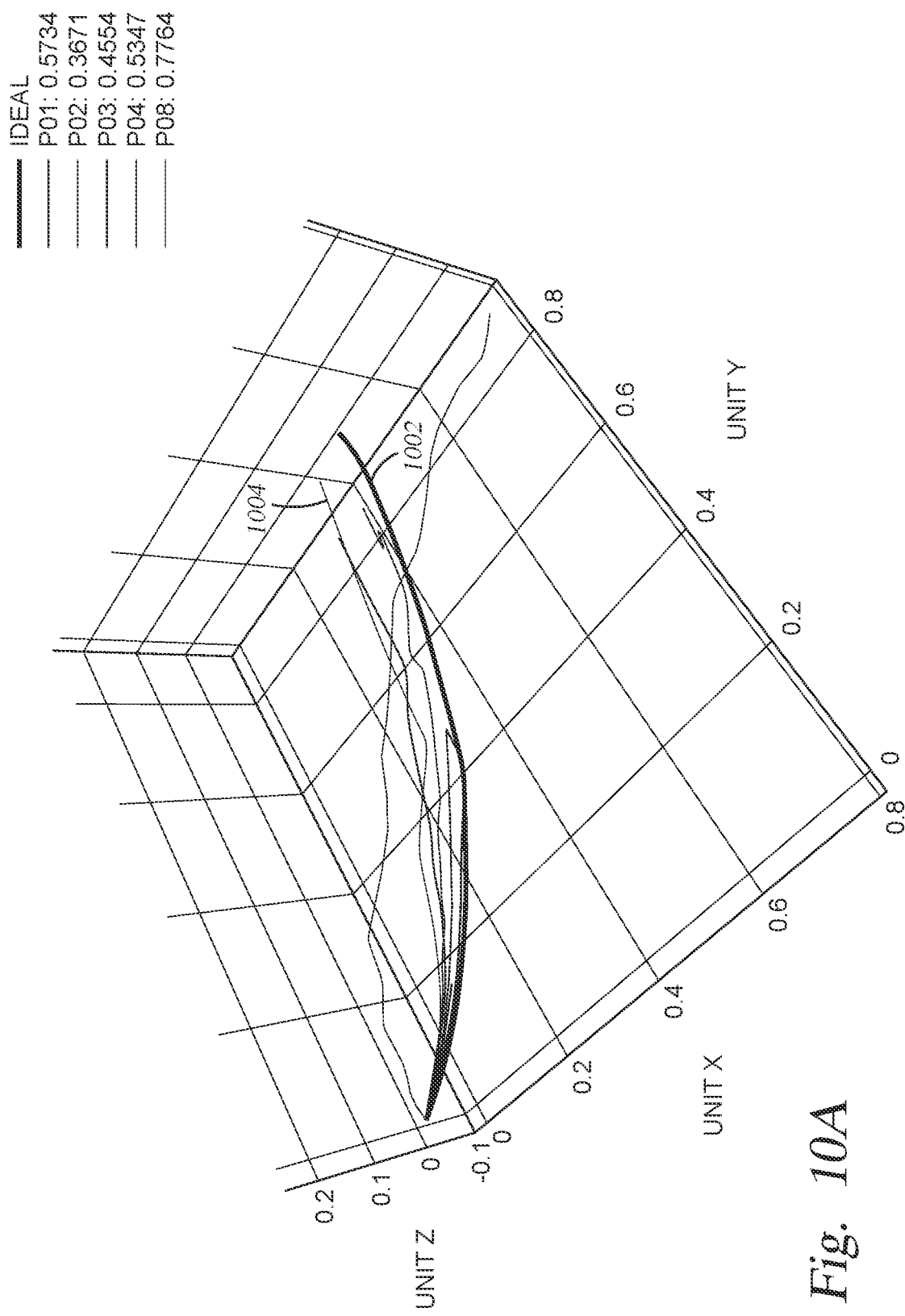
FIGS. 10A and 10B depict examples of augmented vector-defined activity paths.
Figure 10B:
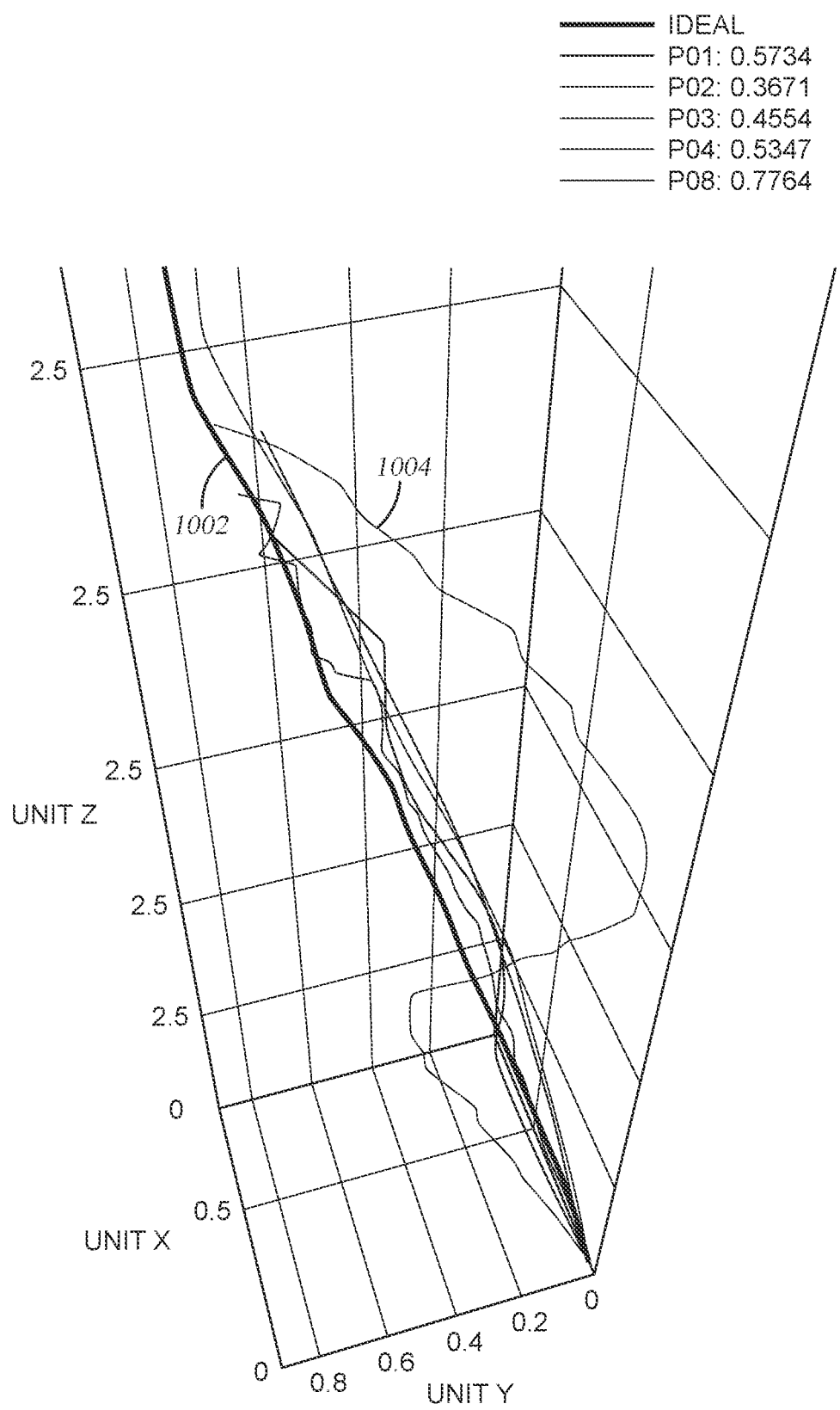

Mathematically, the sequence of these augmented vectors defines a path in a space with an appropriate number of dimensions, this path having the same number of dimensions as the augmented vector, such as shown in FIGS. 10A and 10B from different perspectives. To compute the distance between paths in this space, for example an ideal activity path 1002 and an activity path followed by a specific subject 1004, a distance function (which is a form of path similarity measure) can be defined on this space based on various approaches, such as a Minkowski distance-based metric, a Hausdorff distance, a Frechet distance, and others. Note that individual variables in the vectors may also be scaled relative to the rest, prior to the application of the distance function.

For example, time derived variables can be scaled higher or lower depending on whether the time aspect is more critical or less critical than the spatial aspects of the activity. The same effect can also be achieved by appropriately defining the distance function rather than scaling the elements of the augmented vector.

Example Method of Assessing Performance of a Physical Activity

Figure 11:
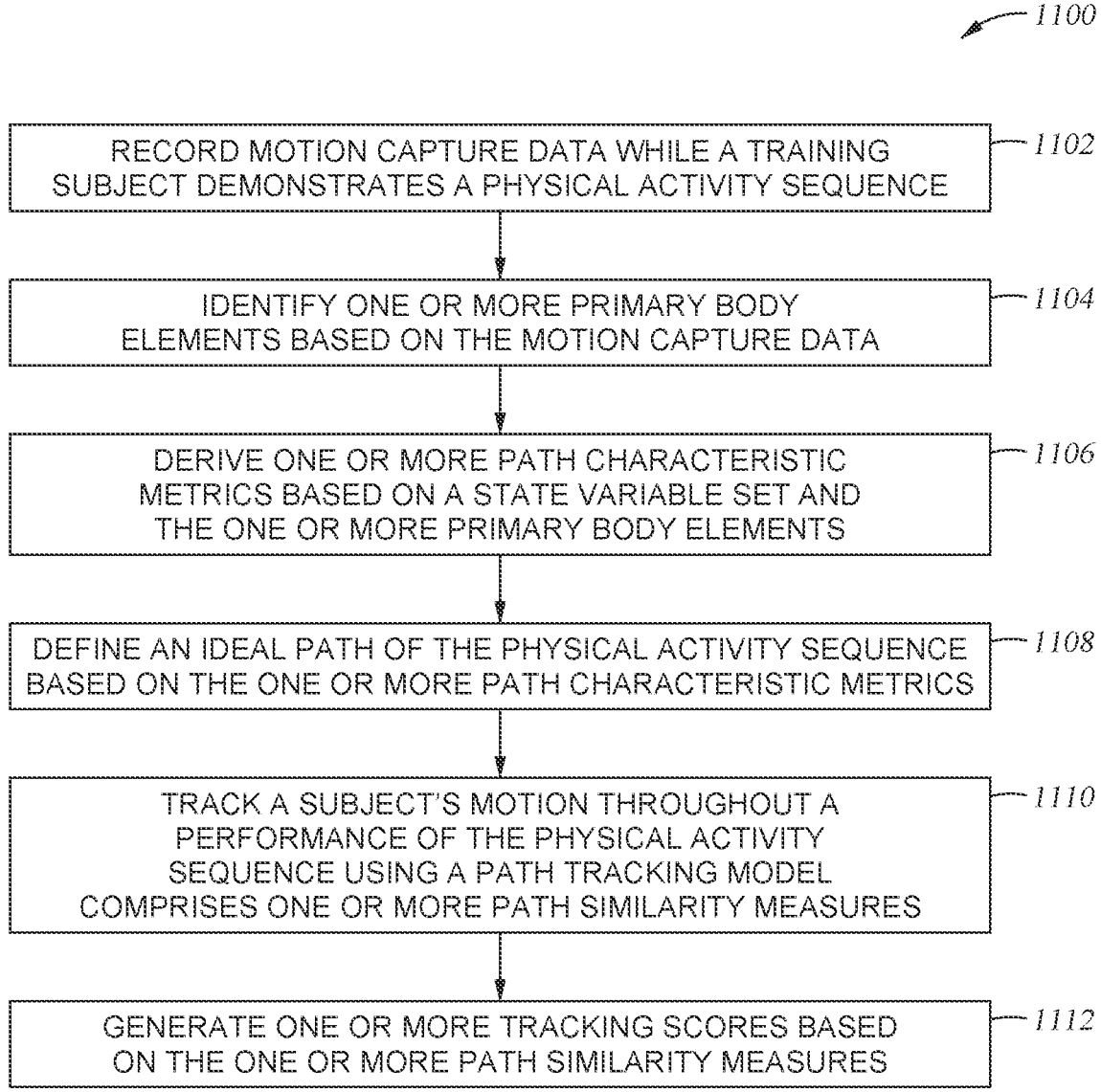
FIG. 11 depicts an example method of assessing the performance of a physical activity.

FIG. 11 depicts an example method 1100 of assessing the performance of a physical activity.

Method 1100 begins at step 1102 with recording motion capture data while a training subject demonstrates a physical activity sequence, such as described above with respect to FIG. 2.

Method 1100 then proceeds to step 1104 with identifying one or more primary body elements based on the motion capture data, such as described above with respect to FIG. 3.

Method 1100 then proceeds to step 1106 with deriving one or more path characteristic metrics based on a state variable set and the one or more primary body elements, wherein the state variable set defines the state of a body at any given time, such as described above with respect to FIG. 2.

Method 1100 then proceeds to step 1108 with defining an ideal activity path of the physical activity sequence based on the one or more path characteristic metrics, such as described above with respect to FIGS. 2 and 7.

Method 1100 then proceeds to step 1110 with tracking a subject's motion throughout a performance of the physical activity sequence using a path tracking model, wherein the path tracking model comprises one or more path similarity measures, such as described above with respect to FIG. 2.

Method 1100 then proceeds to step 1112 with generating one or more tracking scores based on the one or more path similarity measures, such as described above with respect to FIGS. 2 and 9.

In some embodiments, method 1100 further includes determining the similarity of the performance of the physical activity sequence to that of the ideal path for the physical activity sequence based on the tracking scores.

In some embodiments, method 1100 further includes recommending corrective actions to the subject based on the tracking scores.

In some embodiments of method 1100, the primary body elements correspond to limbs of the trainer.

In some embodiments of method 1100, identifying the primary body elements includes: quantifying work performed by a plurality of body elements in the motion capture data; and selecting as primary body elements a subset of the plurality of body elements performing work above a work threshold.

In some embodiments of method 1100, the ideal activity path is further defined based on multiple recorded physical activity sequence samples captured in the motion capture data, such as described above with respect to FIGS. 5-7.

In some embodiments of method 1100, all recorded physical activity sequence samples are normalized with respect to a representation of path completion of the physical activity sequence, such as described above with respect to FIG. 5.

In some embodiments of method 1100, the one or more path characteristic metrics comprise primary body element unit vectors, such as described above with respect to FIGS. 3 and 4.

In some embodiments of method 1100, at least one of the one or more path similarity measures comprises a measure of similarity between curves that takes into account the location and ordering of the points along the curves, for example, like the Frechet distance.

Notably, method 1100 is just one example, and many others are possible as described herein.

Example Processing System

Figure 12:
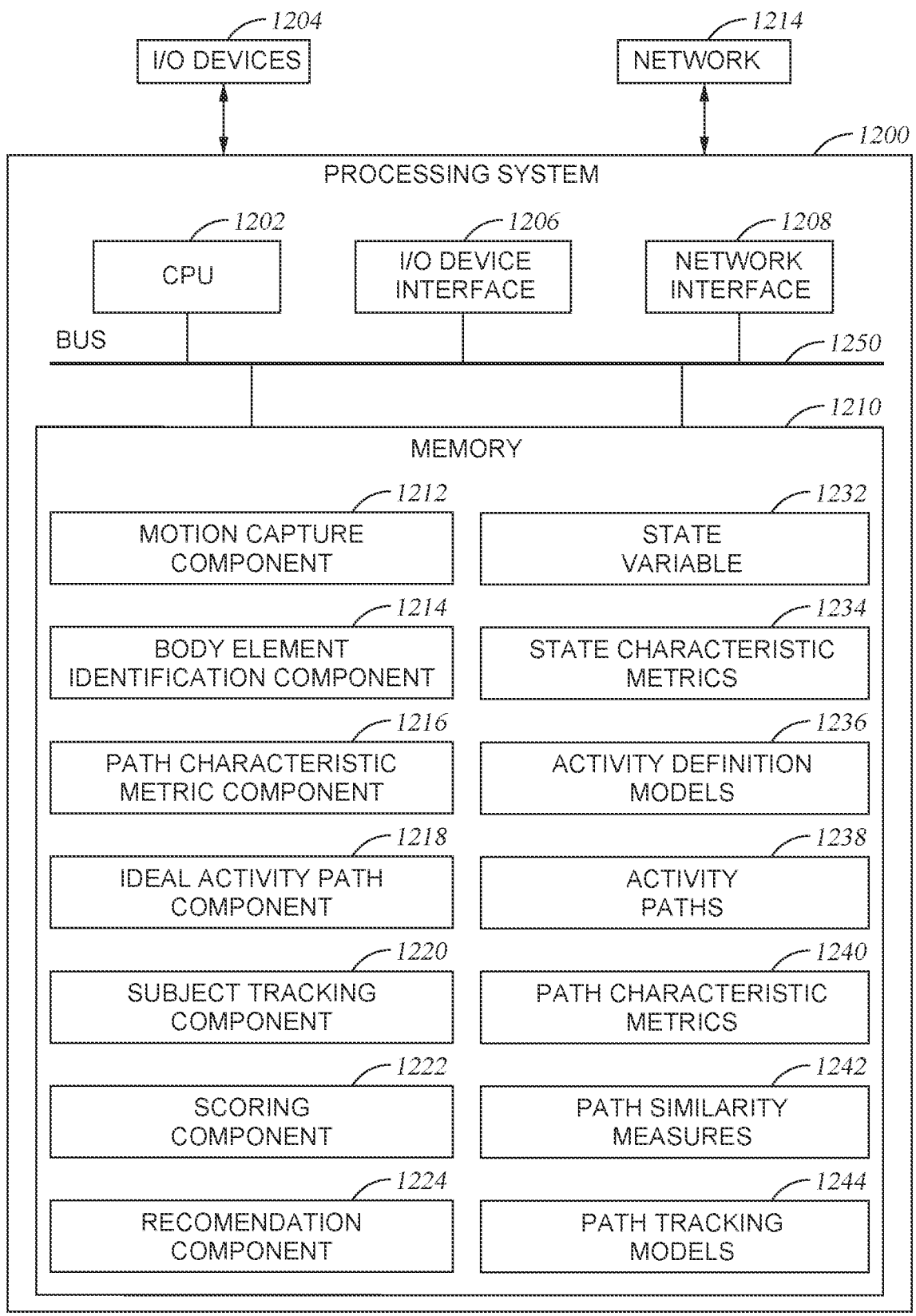
FIG. 12 depicts an example processing system configured to generate and use activity path tracking models.

FIG. 12 depicts an example processing system 1200 configured to generate and use activity path tracking models.

For example, processing system 1200 may be configured to perform one or more aspects of the flows described with respect to FIG. 2 and method 1100 described with respect to FIG. 11.

Processing system 1200 includes a CPU 1202 connected to a data bus 1250. CPU 1202 is configured to process computer-executable instructions, e.g., stored in memory 1210, and to cause processing system 1200 to perform methods as described herein. CPU 1202 is included to be representative of a single CPU, multiple CPUs, a single CPU having multiple processing cores, and other forms of processing architecture capable of executing computer-executable instructions.

Processing system 1200 further includes input/output device(s) 1204, which may include motion capture or tracking devices as described herein, as well as input/output interface(s) 1206, which allow processing system 1200 to interface with input/output devices, such as, for example, keyboards, displays, mouse devices, pen input, motion capture or tracking devices, motion tracking sensors, and other devices that allow for interaction with processing system 1200.

Processing system 1200 further includes network interface 1208, which provides processing system 1200 with access to external networks, such as network 1214.

Processing system 1200 further includes memory 1210, which in this example includes a plurality of components.

For example, memory 1210 includes motion capture component 1212, body element identification component 1214, path characteristic metric component 1216, ideal activity path component 1218, subject tracking component 1220, scoring component 1222, and recommendation component 1224, each of which may be configured to perform various aspects of the methods described herein, including method 1100 described with respect to FIG. 11.

Memory 1210 further includes state variables 1232, state characteristic metrics 1234, activity definition models 1236, activity paths 1238, path characteristic metrics 1240, path similarity measures 1242, and path tracking models 1244, each of which may be configured to support various aspects of the methods described herein, including method 1100 described with respect to FIG. 11.

Note that FIG. 12 depicts various example aspects stored in memory 1210, but others are possible consistent with the systems and methods described herein. Further, while shown as a single memory 1210 in FIG. 12 for simplicity, the various components stored in memory 1210 may be stored in different memories, but all accessible CPU 1202 via internal data connections, such as bus 1250, and external data connections, such as network interface 1208.

Notably, while shown as a single processing system in the example depicted in FIG. 12, other embodiments may include distributed processes that function together as a processing system. For example, the various aspects in memory 1210 may be implemented or stored across a network of processing systems, or in a cloud-based processing system, or in combinations of the same.

For example, a patient may have a client processing system that includes a motion tracking I/O device that captures lives data and feeds it back to a server processing system. Similarly, the patient's client processing system may store path tracking models 1244 locally, which were generated remotely, and which were downloaded to the local client processing system over a network connection, such as the Internet.

Further, processing system 1200 may be configured to function as a training system or a tracking system. Other embodiments of processing systems may be a training system only, or a tracking system only. For example, patients may receive only tracking systems.

In general, processing system 1200 is just one possible embodiment, and the various aspects of processing system 1200 may be distributed across a plurality of devices, may be omitted, or added as necessary for any of the particular functions or methods described herein.

Alternative Implementations and Other Capabilities

Though a few example implementations are described herein, there are various ways of implementing the methods described herein.

Path tracking models (e.g., 218 in FIG. 2) may also be used to detect erroneous motions one wishes to avoid during a physical activity sequence. To this end, an activity path representing an erroneous/non-ideal activity sequence can be calculated using data from recorded non-ideal activity motion capture data samples. Then a path tracking model can be formulated to identify the equivalence of the subject's motions to this non-ideal activity path. The resulting tracking score can be used to detect when the subject is performing the activity in this non-ideal manner. These erroneous/non-ideal motions may include motions that could potentially result in injury or are engaging incorrect body regions.

Patient screening may be performed with the help of a path tracking model. Patients with issues of limited range of motion or inflexibility of certain joints associated with common ailments, may perform activities in a distinguishable manner. Specific idealized paths, used for screening, can be formulated based on motion capture data samples from subjects of a common condition to detect this specific condition. When live tracking, the subject's similarity to this screening idealized path can be calculated to assess the potential for the subject to possess the condition of interest.

Activity sequence progression can also be calculated using a process of matching the subject's current state to the best matching state along the idealized path. The index of the best matching state along the idealized path can be used to estimate the percentage of completion of the associated activity path. This may be used to provide the subject with live feedback of their progression performing a prescribed activity.

The methods described herein may further be configured to track compliance and potential activity form degradation throughout the course of performing a set of prescribed activity sequences. Tracking score values may be used to determine if the patient is truly demonstrating the correct motion required for the activity during each repetition in the set. Tracking score value variations over the course of a set of activity sequence repetitions may be monitored and ultimately used to make alterations to the prescribed activity.

Formulation of path tracking models and ideal activity paths may generally require quantified pose information. This data may come from varying sources or methods other than a motion capture source as previously described. For example, an alternative motion capture device may include optical camera systems with image processing, marker based tracking systems with various marker (active, passive, semi-passive, modulated) and detector (optical, radio frequency) types, depth camera systems with object recognition algorithms, inertial measurement units, mechanical exoskeleton motion capture systems, or magnetic flux measurement systems. Other potential sources include, but are not limited to, data extracted from inertia-measurement-units (IMUs) and image processing methods that compare sequential images to determine differences. Depth cameras and/or point cloud mapping can also be used to extract information on varying states.

Path tracking models can also be formulated from data expressed in various other coordinate spaces rather than those discussed herein. For example, two-dimensional (2D)

data could be extracted from image processing techniques, or 3D motion capture devices may project tracking data onto a 2D plane.

Path tracking models may be time-invariant, as described above, but are nevertheless fully capable of tracking and comparing activity sequence timing. Ideal timing can be extracted from the recorded motion capture data to determine the desired rate of transition between key states. These transition periods between key states can be identified using classifiers within an activity definition model. With discrete boundaries established between key states and transition zones, time information can be recorded and binned into associated key state/transition regions. Subject timing during key state transitions can be compared to that from the idealized activity motion recorded during path tracking model formulation.

Various statistical and comparative methods can be applied for path similarity assessment and implemented for use as a path similarity measures. These include, but are not limited to, root mean square deviation, Minkowski distance based functions, Frechet distance, Hausdorff distance, signal cross-correlation, cross-covariance, dynamic time warping, and others.

For idealized path formulation, the activity sequence can be segmented into sections between each key state in the activity (as described above) to create a piecewise idealized path for the activity sequence. An alternative implementation is also possible where a continuous idealized path can be calculated for the full activity sequence.

Use of path tracking models for physical activity tracking has been described herein for rehabilitation applications and can be applied to many other tasks. This includes biomechanical analysis of physical activity training and sport science research, such as training proper form or detection of critical movements. This method also has potential applications in clinical sciences such as the analysis of posture, balance, gait, and motor control. The same approach can be used for gesture/pose recognition and detection in virtual reality, gaming applications, robotics, manufacturing applications, and ergonomic studies. Path comparative models can also be applied in psychological studies for analysis on behavioral and physical response.

Example Clauses

Clause 1: A method for assessing the performance of a physical activity, comprising: recording motion capture data while a training subject demonstrates a physical activity sequence; identifying one or more primary body elements based on the motion capture data; deriving one or more path characteristic metrics based on a state variable set and the one or more primary body elements, wherein the state variable set defines the state of a body at any given time; and defining an ideal activity path of the physical activity sequence based on the one or more path characteristic metrics.

Clause 2: The method of Clause 1, further comprising: tracking a subject's motion throughout a performance of the physical activity sequence using a path tracking model, wherein the path tracking model comprises one or more path similarity measures; and generating one or more tracking scores based on the one or more path similarity measures.

Clause 3: The method of Clause 2, further comprising: determining the similarity of the performance of the physical activity sequence to that of the ideal activity path for the physical activity sequence based on the tracking scores.

Clause 4: The method of Clause 3, further comprising: recommending corrective actions to the subject based on the tracking scores.

Clause 5: The method of any one of Clauses 1-4, wherein the one or more primary body elements correspond to limbs of the training subject.

Clause 6: The method of any one of Clauses 1-5, wherein identifying the one or more primary body elements comprises: quantifying work performed by a plurality of body elements in the motion capture data; and selecting as the one or more primary body elements a subset of the plurality of body elements performing work above a work threshold.

Clause 7: The method of any one of Clauses 1-6, wherein the ideal activity path is further defined based on multiple recorded physical activity sequence samples captured in the motion capture data.

Clause 8: The method of Clause 7, wherein all recorded physical activity sequence samples are normalized with respect to a representation of path completion of the physical activity sequence.

Clause 9: The method of any one of Clauses 1-8, wherein the one or more path characteristic metrics comprise primary body element unit vectors.

Clause 10: The method of Clause 2, wherein at least one of the one or more path similarity measures comprises a measure of similarity between curves that takes into account the location and ordering of the points along the curves.

Clause 11: A processing system, comprising: a memory comprising computer-executable instructions; and one or more processors configured to execute the computer-executable instructions and cause the processing system to perform a method in accordance with any one of Clauses 1-10.

Clause 12: A non-transitory computer-readable medium comprising computer-executable instructions that, when executed by one or more processors of a processing system, cause the processing system to perform a method in accordance with any one of Clauses 1-10.

Clause 13: A computer program product embodied on a computer readable storage medium comprising code for performing a method in accordance with any one of Clauses 1-10.

Additional Considerations

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

We claim:

1. An apparatus comprising:
   at least one processor;
   a memory coupled to the at least one processor, the memory comprising instructions that, when executed by the at least one processor, cause the at least one processor to:
   access training motion capture data of a plurality of samples of a body of at least one training subject performing a physical activity sequence comprising a sequence of states,
   determine at least one primary body element for the physical activity sequence, and
   determine a path tracking model configured to numerically represent a path of the at least one primary body element as the body performs the physical activity sequence, the path tracking model determined via:
   determining at least one path characteristic metric of the at least one primary body element during each of the sequence of states, the at least one path characteristic metric comprising a numeric variable defining state information of the at least one primary body element during one of the sequence of states, and
   determining an ideal activity path of the physical activity sequence, the ideal activity path comprising an ordered sequence of the at least one path characteristic metric during the sequence of states normalized with respect to time for each of the plurality of samples to associate the ideal activity path with a time component expressed as a percentage of completion.

2. The apparatus of claim 1, the state information of the at least one primary body element comprising at least one of a position or an orientation of the at least one primary body element.

3. The apparatus of claim 1, the instructions, when executed by the at least one processor, to cause the at least one processor to:
   quantify work performed by a plurality of body elements in the training motion capture data, and
   select at least one of the plurality of body elements performing work above a threshold as the at least one primary body element.

4. The apparatus of claim 1, the instructions, when executed by the at least one processor, to cause the at least one processor to determine a plurality of key states of the physical activity sequence based on the training motion capture data, each of the plurality of key states comprising a specific state that in-part defines the physical activity sequence.

5. The apparatus of claim 4, the ideal activity path comprising a sequence of the plurality of key states.

6. The apparatus of claim 1, the path tracking model comprising at least one path similarity measure numerically quantifying a similarity between an actual activity path and the ideal activity path.

7. The apparatus of claim 1, the at least one path characteristic metric comprising a unit vector of the primary body element.

8. The apparatus of claim 1, the at least one path characteristic metric associated with temporal information indicating an amount of time to complete at least a portion of the ideal activity path.

9. The apparatus of claim 1, the ideal activity path comprising a multi-dimensional path of the at least one primary body element between each of the sequence of states, each dimension of the multi-dimensional path comprising a spatial dimension associated with the at least one primary body element.

10. The apparatus of claim 1, the ideal activity path further defined based on multiple recorded physical activity sequence samples of different performances of the physical activity sequence captured in the training motion capture data.

11. A computer-implemented method, comprising, via at least one processor of a computing device:
  accessing training motion capture data of a plurality of samples of a body of at least one training subject performing a physical activity sequence comprising a sequence of states,
  determining at least one primary body element for the physical activity sequence, and
  determining a path tracking model configured to numerically represent a path of the at least one primary body element as the body performs the physical activity sequence, the path tracking model determined via:
    determining at least one path characteristic metric of the at least one primary body element during each of the sequence of states, the at least one path characteristic metric comprising a numeric variable defining state information of the at least one primary body element during one of the sequence of states, and
    determining an ideal activity path of the physical activity sequence, the ideal activity path comprising an ordered sequence of the at least one path characteristic metric during the sequence of states normalized with respect to time for each of the plurality of samples to associate the ideal activity path with a time component expressed as a percentage of completion.

12. The method of claim 11, the state information of the at least one primary body element comprising at least one of a position or an orientation of the at least one primary body element.

13. The method of claim 11, comprising:
  quantifying work performed by a plurality of body elements in the training motion capture data, and
  selecting at least one of the plurality of body elements performing work above a threshold as the at least one primary body element.

14. The method of claim 11, comprising determining a plurality of key states of the physical activity sequence based on the training motion capture data, each of the plurality of key states comprising a specific state that in-part defines the physical activity sequence.

15. The method of claim 14, the ideal activity path comprising a sequence of the plurality of key states.

16. The method of claim 11, the path tracking model comprising at least one path similarity measure numerically quantifying a similarity between an actual activity path and the ideal activity path.

17. The method of claim 11, the at least one path characteristic metric comprising a unit vector of the primary body element.

18. The method of claim 11, the at least one path characteristic metric associated with temporal information indicating an amount of time to complete at least a portion of the ideal activity path.

19. The method of claim 11, the ideal activity path comprising a multi-dimensional path of the at least one primary body element between each of the sequence of states, each dimension of the multi-dimensional path comprising a spatial dimension associated with the at least one primary body element.

20. The method of claim 11, the ideal activity path further defined based on multiple recorded physical activity sequence samples of different performances of the physical activity sequence captured in the training motion capture data.

* * * * *